US00PP25055P2

(12) United States Plant Patent
Isobe

(10) Patent No.: US PP25,055 P2
(45) Date of Patent: Nov. 11, 2014

(54) ***PETUNIA* PLANT NAMED 'SUNSURF EJIUSA'**

(50) Latin Name: *Petunia×hybrida*
Varietal Denomination: Sunsurf Ejiusa

(71) Applicant: Yasuko Isobe, Shiga (JP)

(72) Inventor: Yasuko Isobe, Shiga (JP)

(73) Assignee: Suntory Flowers Limited, Tokyo (JP)

( * ) Notice: Subject to any disclaimer, the term of this patent is extended or adjusted under 35 U.S.C. 154(b) by 110 days.

(21) Appl. No.: 13/694,498

(22) Filed: Dec. 6, 2012

(51) Int. Cl.
*A01H 5/00* (2006.01)

(52) U.S. Cl.
USPC ..... Plt./356.13; Plt./356.1; Plt./356.14

(58) Field of Classification Search
USPC ..... Plt./356.1, 356.13, 356.14
See application file for complete search history.

*Primary Examiner* — Susan McCormick Ewoldt
(74) *Attorney, Agent, or Firm* — C. A. Whealy

(57) ABSTRACT

A new and distinct cultivar of *Petunia* plant named 'Sunsurf Ejiusa', characterized by its compact and uniformly mounding plant habit; vigorous growth habit; freely branching habit; early and freely flowering habit; long flowering period; light and bright yellow green bi-colored flowers; and good garden performance.

1 Drawing Sheet

Botanical designation: *Petunia×hybrida.*
Cultivar denomination: 'SUNSURF EJIUSA'.

BACKGROUND OF THE INVENTION

The present invention relates to a new and distinct cultivar of *Petunia* plant, botanically known as *Petunia×hybrida* and hereinafter referred to by the name 'Sunsurf Ejiusa'.

The new *Petunia* plant is a product of a planned breeding program conducted by the Inventor in Higashiomi, Shiga, Japan. The objective of the breeding program is to create new compact, freely branching and freely flowering *Petunia* plants with uniformly mounding habit and attractive flower coloration.

The new *Petunia* plant originated from a cross-pollination made by the Inventor in July, 2008 in Higashiomi, Shiga, Japan of a proprietary selection of *Petunia×hybrida* identified as code number Px2982-01, not patented, as the female, or seed, parent with a proprietary selection of *Petunia×hybrida* identified as code number Px3015-03, not patented, as the male, or pollen, parent. The new *Petunia* plant was discovered and selected by the Inventor as a single flowering plant within the progeny of the stated cross-pollination in a controlled greenhouse environment in Higashiomi, Shiga, Japan in November, 2009.

Asexual reproduction of the new *Petunia* plant by terminal cuttings in a controlled greenhouse environment in Higashiomi, Shiga, Japan since November, 2009 has shown that the unique features of this new *Petunia* plant are stable and reproduced true to type in successive generations.

SUMMARY OF THE INVENTION

Plants of the new *Petunia* have not been observed under all possible environmental conditions and cultural conditions. The phenotype may vary somewhat with variations in environmental conditions such as temperature and light intensity without, however, any variance in genotype.

The following traits have been repeatedly observed and are determined to be the unique characteristics of 'Sunsurf Ejiusa'. These characteristics in combination distinguish 'Sunsurf Ejiusa' as a new and distinct *Petunia* plant:

1. Compact and uniformly mounding plant habit.
2. Vigorous growth habit.
3. Freely branching habit.
4. Early and freely flowering habit.
5. Long flowering period.
6. Light and bright yellow green bi-colored flowers.
7. Good garden performance.

Plants of the new *Petunia* can be compared to plants of the female parent selection. Plants of the new *Petunia* differ primarily from plants of the female parent selection in flower size as plants of the female parent selection have larger flowers.

Plants of the new *Petunia* can be compared to plants of the male parent selection. Plants of the new *Petunia* differ primarily from plants of the male parent selection in the following characteristics:

1. Plants of the new *Petunia* are broader than plants of the male parent selection.
2. Plants of the new *Petunia* are more mounding than and not as trailing as plants of the male parent selection.
3. Plants of the new *Petunia* have smaller flowers than plants of the male parent selection.

Plants of the new *Petunia* can also be compared to plants of the *Petunia* 'Sunsurf Kuritora', disclosed in U.S. Plant Pat. No. 23,969. In side-by-side comparisons conducted in Higashiomi, Shiga, Japan, plants of the new *Petunia* and 'Sunsurf Kuritora' differed primarily in the following characteristics:

1. Plants of the new *Petunia* were taller than plants of 'Sunsurf Kuritora'.
2. Plants of the new *Petunia* had lighter green-colored leaves than plants of 'Sunsurf Kuritora'.
3. Plants of the new *Petunia* had smaller flowers than plants of 'Sunsurf Kuritora'.
4. Plants of the new *Petunia* and 'Sunsurf Kuritora' differed in flower color as plants of 'Sunsurf Kuritora' had pale yellow-colored flowers.

BRIEF DESCRIPTION OF THE PHOTOGRAPHS

The accompanying colored photographs illustrate the overall appearance of the new *Petunia* plant showing the colors as true as it is reasonably possible to obtain in colored reproductions of this type. Colors in the photographs may differ slightly from the color values cited in the detailed botanical description which accurately describe the colors of the new *Petunia* plant.

The photograph at the top of the sheet comprises a side perspective view of a typical flowering plant of 'Sunsurf Ejiusa' grown in a container.

The photograph at the bottom of the sheet is a close-up view of a typical flowering plant of 'Sunsurf Ejiusa'.

DETAILED BOTANICAL DESCRIPTION

The aforementioned photographs and following observations, measurements and values describe plants grown during the late spring in 15-cm containers in an outdoor nursery in Higashiomi, Shiga, Japan and under cultural practices typical of commercial *Petunia* production. During the production of the plants, day temperatures averaged 23° C. and night temperatures averaged 13° C. Plants were two months old when the photographs were taken and five months old when the description was taken. In the following description, color references are made to The Royal Horticultural Society Colour Chart, 2007 Edition, except where general terms of ordinary dictionary significance are used.

Botanical classification: *Petunia×hybrida* 'Sunsurf Ejiusa'.

Parentage:

*Female, or seed, parent*.—Proprietary selection of *Petunia×hybrida* identified as code number Px2982-01, not patented.

*Male, or pollen, parent*.—Proprietary selection of *Petunia×hybrida* identified as code number Px3015-03, not patented.

Propagation:

*Type*.—By terminal cuttings.

*Time to initiate roots, summer and winter*.—About one week at temperatures of about 15° C. to 20° C.

*Time to produce a rooted young plant, summer and winter*.—About three weeks at temperatures of about 15° C. to 20° C.

*Root description*.—Fibrous; white in color.

*Rooting habit*.—Freely branching; dense.

Plant description:

*Plant form and growth habit*.—Compact and uniformly mounding plant habit; freely branching habit with numerous lateral branches developing per plant; pinching enhances lateral branch development; vigorous growth habit.

*Plant height*.—About 29.3 cm.

*Plant diameter*.—About 54.6 cm.

Lateral branch description:

*Length*.—About 36.8 cm.

*Diameter*.—About 3.4 mm.

*Internode length*.—About 2.4 cm.

*Strength*.—Strong, flexible.

*Aspect*.—Upright to outwardly.

*Texture*.—Densely pubescent; viscid.

*Color*.—Close to 144A.

Foliage description:

*Arrangement*.—Alternate, simple.

*Length*.—About 3.2 cm.

*Width*.—About 1.8 cm.

*Shape*.—Elliptic.

*Apex*.—Broadly acute.

*Base*.—Cuneate.

*Margin*.—Entire; slightly undulate.

*Texture, upper and lower surfaces*.—Pubescent.

*Venation pattern*.—Pinnate; reticulate.

*Color*.—Developing and fully expanded leaves, upper surface: Close to 144A; venation, close to 144C. Developing and fully expanded leaves, lower surface: Close to 144B; venation, close to 144C.

*Petioles*.—Length: About 3.5 mm. Diameter: About 0.4 mm. Texture, upper and lower surfaces: Densely pubescent. Color, upper and lower surfaces: Close to 144C.

Flower description:

*Flower arrangement and habit*.—Single funnelform flowers arising from upper leaf axils; freely flowering habit with usually about 85 flowers developing per plant; flowers face upright to outwardly.

*Fragrance*.—Not detected.

*Natural flowering season*.—Early flowering habit, plants of the new *Petunia* initiate and develop flowers about three to four weeks after planting; long flowering period; flowering commences naturally during the spring and plants flower continuously throughout the summer until late autumn in Japan.

*Flower longevity*.—Individual flowers last about seven to ten days on the plant; flowers not persistent.

*Flower diameter*.—About 3.3 cm.

*Flower length (depth)*.—About 4.1 cm.

*Throat diameter*.—About 1.1 cm.

*Tube diameter, base*.—About 3.1 mm.

*Tube length*.—About 2.7 cm.

*Flower buds*.—Length: About 3.2 cm. Diameter: About 9 mm. Shape: Cylindrical. Color: Close to 145B; towards the apex, close to 145A.

*Corolla*.—Arrangement: Five petals fused at the base and opening into a flared trumpet. Petal length from throat: About 1.2 cm. Petal width: About 1.6 cm. Petal shape: Spatulate. Petal apex: Mucronate. Petal margin: Entire. Petal texture, upper and lower surfaces: Smooth, glabrous. Throat texture: Smooth, glabrous. Tube texture: Pubescent. Color: Petal, when opening and fully opened, upper surface: Close to 149D; towards the margins, close to 149A; venation, close to 149A. Petal, when opening and fully opened, lower surface: Close to 149D; towards the margins, close to 149A; venation, close to 149A. Throat: Close to 149D; venation, close to 149A. Tube: Close to 149D; venation, close to 149A.

*Calyx*.—Arrangement: One star-shaped calyx tube with five sepals in a single whorl and fused at the base. Sepal length: About 1.4 cm. Sepal width: About 2.9 mm. Sepal shape: Narrowly elliptic. Sepal apex: Obtuse. Sepal margin: Entire. Sepal texture, upper and lower surfaces: Pubescent. Color: Developing and fully developed sepals, upper surface: Close to 144A. Developing and fully developed sepals, lower surface: Close to 144A.

*Peduncles*.—Length: About 2 cm. Diameter: About 1.5 mm. Strength: Strong. Texture: Densely pubescent. Color: Close to 143C.

*Reproductive organs*.—Stamens: Quantity per flower: Five. Stamen length: About 1.8 cm to 2 cm. Anther shape: Ellipsoidal. Anther size: About 2.2 mm by 2.9 mm. Anther color: Close to 2D. Pollen amount: Moderate. Pollen color: Close to 2D. Pistils: Quantity per flower: One. Pistil length: About 2.1 cm. Style color:

Close to 145C. Stigma shape: Transversely ellipsoidal. Stigma color: Close to 145B. Ovary color: Close to 143C. Seeds and fruits: Seed and fruit development have not been observed on plants of the new *Petunia*.

Garden performance: Plants of the new *Petunia* have been observed to have good garden performance and to tolerate rain, wind and temperatures ranging from about 5° C. to about 35° C.

Pathogen & pest resistance: Plants of the new *Petunia* have not been observed to be resistant to pathogens and pests common to *Petunia* plants.

It is claimed:

1. A new and distinct *Petunia* plant named 'Sunsurf Ejiusa' as illustrated and described.

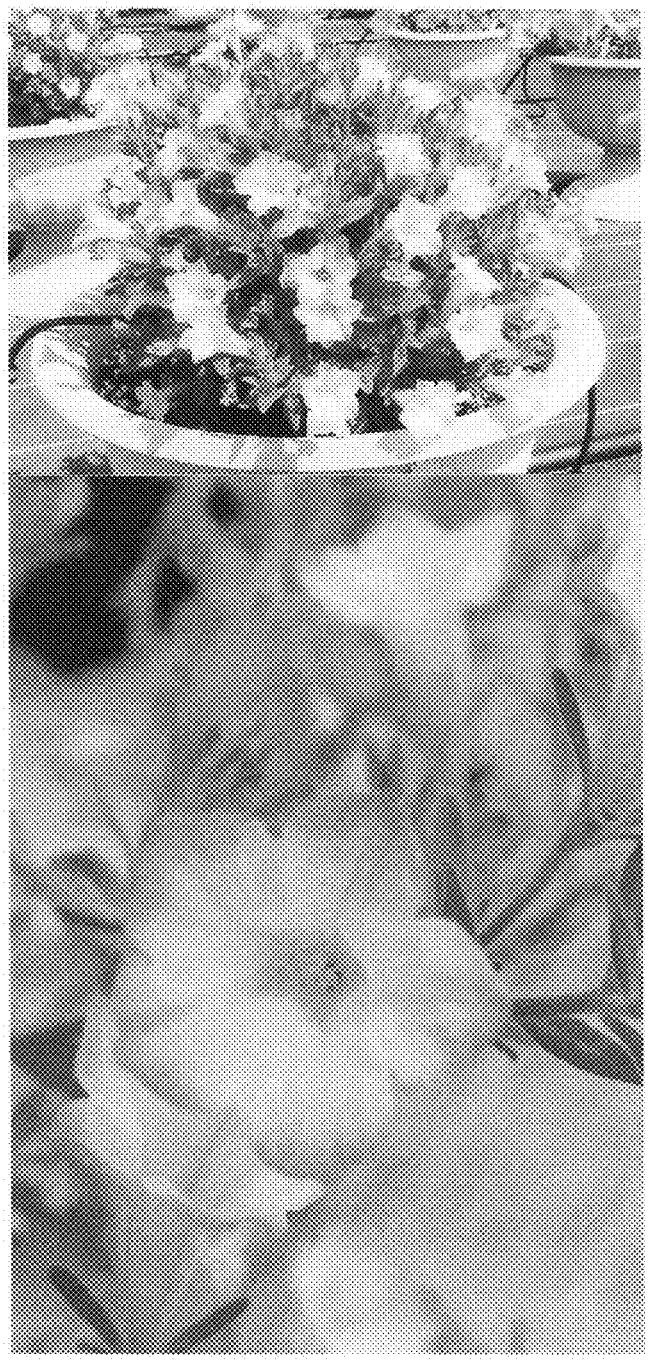

* * * * *